US010499989B2

United States Patent
Brannan et al.

(10) Patent No.: US 10,499,989 B2
(45) Date of Patent: *Dec. 10, 2019

(54) NARROW GAUGE HIGH STRENGTH CHOKED WET TIP MICROWAVE ABLATION ANTENNA

(71) Applicant: COVIDIEN LP, Mansfield, MA (US)

(72) Inventors: Joseph D. Brannan, Lyons, CO (US); Kenlyn S. Bonn, Lakewood, CO (US)

(73) Assignee: COVIDIEN LP, Mansfield, MA (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/606,487

(22) Filed: May 26, 2017

(65) Prior Publication Data

US 2017/0265941 A1     Sep. 21, 2017

Related U.S. Application Data

(63) Continuation of application No. 14/931,922, filed on Nov. 4, 2015, now Pat. No. 9,662,172, which is a
(Continued)

(51) Int. Cl.
*A61B 18/18* (2006.01)
*A61B 18/14* (2006.01)
*A61B 18/00* (2006.01)

(52) U.S. Cl.
CPC .......... *A61B 18/1815* (2013.01); *A61B 18/14* (2013.01); *A61B 18/18* (2013.01);
(Continued)

(58) Field of Classification Search
CPC ..... A61B 18/1815; A61B 18/14; A61B 18/18; A61B 2018/1869; A61B 2018/1823;
(Continued)

(56) References Cited

U.S. PATENT DOCUMENTS 3,631,363 A    12/1971  Miller
D223,367 S      4/1972  Kountz
(Continued)

FOREIGN PATENT DOCUMENTS

CN    1103807 C    3/2003
DE     390937 C    3/1924
(Continued)

OTHER PUBLICATIONS

Australian Office Action dated Oct. 11, 2017 issued in Australian Application No. 2017202181.
(Continued)

*Primary Examiner* — Bradley J Osinski
*Assistant Examiner* — Hamza A Darb
(74) *Attorney, Agent, or Firm* — Carter, DeLuca & Farrell LLP (57) ABSTRACT

An electromagnetic surgical ablation probe having a coaxial feedline and cooling chamber is disclosed. The disclosed probe includes a dipole antenna arrangement having a radiating section, a distal tip coupled to a distal end of the radiating section, and a ring-like balun short, or choke, which may control a radiation pattern of the probe. A conductive tube disposed coaxially around the balun short includes at least one fluid conduit which provides coolant, such as dionized water, to a cooling chamber defined within the probe. A radiofrequency transparent catheter forms an outer surface of the probe and may include a lubricious coating.

14 Claims, 6 Drawing Sheets

Related U.S. Application Data continuation of application No. 13/657,638, filed on Oct. 22, 2012, now Pat. No. 9,192,437, which is a continuation of application No. 12/472,831, filed on May 27, 2009, now Pat. No. 8,292,881.

(52) U.S. Cl.
CPC .............. *A61B 2018/00023* (2013.01); *A61B 2018/00577* (2013.01); *A61B 2018/1823* (2013.01); *A61B 2018/1869* (2013.01); *Y10T 29/49117* (2015.01)

(58) Field of Classification Search
CPC ........... A61B 2018/00577; A61B 2018/00023; Y10T 29/49117
See application file for complete search history.

(56) References Cited

U.S. PATENT DOCUMENTS

| | | |
|---|---|---|
| D263,020 S | 2/1982 | Rau, III |
| D266,842 S | 11/1982 | Villers et al. |
| 4,397,313 A | 8/1983 | Vaguine |
| 4,462,412 A | 7/1984 | Turner |
| D278,306 S | 4/1985 | McIntosh |
| 4,572,190 A | 2/1986 | Azam et al. |
| 4,674,481 A | 6/1987 | Boddie, Jr. et al. |
| 4,700,716 A | 10/1987 | Kasevich et al. |
| D295,893 S | 5/1988 | Sharkany et al. |
| D295,894 S | 5/1988 | Sharkany et al. |
| 4,776,086 A | 10/1988 | Kasevich et al. |
| 4,798,215 A | 1/1989 | Turner |
| 4,823,812 A | 4/1989 | Eshel et al. |
| 4,825,880 A | 5/1989 | Stauffer et al. |
| 4,940,991 A | 7/1990 | Sheriff |
| 5,057,106 A | 10/1991 | Kasevich et al. |
| 5,097,844 A | 3/1992 | Turner |
| 5,197,468 A | 3/1993 | Proctor et al. |
| 5,301,687 A | 4/1994 | Wong et al. |
| D354,218 S | 1/1995 | Van de Peer |
| 5,417,210 A | 5/1995 | Funda et al. |
| 5,484,398 A | 1/1996 | Stoddard |
| 5,902,251 A | 5/1999 | vanHooydonk |
| 5,938,692 A | 8/1999 | Rudie |
| 5,961,871 A | 10/1999 | Bible et al. |
| 6,016,452 A | 1/2000 | Kasevich |
| 6,019,757 A | 2/2000 | Scheldrup |
| 6,031,375 A | 2/2000 | Atalar et al. |
| 6,032,078 A | 2/2000 | Rudie |
| 6,047,216 A | 4/2000 | Carl et al. |
| D424,693 S | 5/2000 | Pruter |
| D424,694 S | 5/2000 | Tetzlaff et al. |
| D425,201 S | 5/2000 | Tetzlaff et al. |
| 6,223,086 B1 | 4/2001 | Carl et al. |
| 6,226,553 B1 | 5/2001 | Carl et al. |
| 6,230,060 B1 | 5/2001 | Mawhinney |
| D449,886 S | 10/2001 | Tetzlaff et al. |
| 6,375,606 B1 | 4/2002 | Garibaldi et al. |
| D457,958 S | 5/2002 | Dycus et al. |
| D457,959 S | 5/2002 | Tetzlaff et al. |
| 6,398,781 B1 | 6/2002 | Goble et al. |
| 6,451,015 B1 | 9/2002 | Rittman, III et al. |
| 6,496,736 B1 | 12/2002 | Carl et al. |
| 6,547,786 B1 | 4/2003 | Goble |
| 6,582,427 B1 | 6/2003 | Goble et al. |
| 6,589,234 B2 | 7/2003 | Lalonde et al. |
| 6,603,994 B2 | 8/2003 | Wallace et al. |
| 6,606,513 B2 | 8/2003 | Lardo et al. |
| D487,039 S | 2/2004 | Webster et al. |
| 6,725,080 B2 | 4/2004 | Melkent et al. |
| 6,758,846 B2 | 7/2004 | Goble et al. |
| D496,997 S | 10/2004 | Dycus et al. |
| D499,181 S | 11/2004 | Dycus et al. |
| 6,878,147 B2 | 4/2005 | Prakash et al. |
| 6,898,454 B2 | 5/2005 | Atalar et al. |
| D525,361 S | 7/2006 | Hushka |
| D531,311 S | 10/2006 | Guerra et al. |
| 7,128,739 B2 | 10/2006 | Prakash et al. |
| D533,942 S | 12/2006 | Kerr et al. |
| 7,147,632 B2 | 12/2006 | Prakash et al. |
| D535,027 S | 1/2007 | James et al. |
| D541,418 S | 4/2007 | Schechter et al. |
| D541,938 S | 5/2007 | Kerr et al. |
| 7,241,293 B2 | 7/2007 | Davison |
| 7,311,703 B2 | 12/2007 | Turovskiy et al. |
| 7,318,824 B2 | 1/2008 | Prakash et al. |
| 7,326,201 B2 | 2/2008 | Fjield et al. |
| D564,662 S | 3/2008 | Moses et al. |
| D576,932 S | 9/2008 | Strehler |
| 7,439,736 B2 | 10/2008 | Meaney et al. |
| 7,467,015 B2 | 12/2008 | van der Weide |
| D594,736 S | 6/2009 | Esjunin |
| D594,737 S | 6/2009 | Kelly et al. |
| 7,565,207 B2 | 7/2009 | Turner et al. |
| D606,203 S | 12/2009 | Husheer et al. |
| 7,642,451 B2 | 1/2010 | Bonn |
| D613,412 S | 4/2010 | DeCarlo |
| 7,875,024 B2 | 1/2011 | Turovskiy et al. |
| D634,010 S | 3/2011 | DeCarlo |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |
| 8,216,227 B2 | 7/2012 | Podhajsky |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,292,880 B2 | 10/2012 | Prakash et al. |
| 8,292,881 B2 * | 10/2012 | Brannan ................ A61B 18/18 606/33 |
| 8,328,799 B2 | 12/2012 | Brannan |
| 8,328,800 B2 | 12/2012 | Brannan |
| 8,328,801 B2 | 12/2012 | Brannan |
| 8,343,145 B2 | 1/2013 | Brannan |
| 8,343,149 B2 | 1/2013 | Rossetto et al. |
| 8,353,902 B2 | 1/2013 | Prakash |
| 8,353,903 B2 | 1/2013 | Podhajsky |
| 8,355,803 B2 | 1/2013 | Bonn et al. |
| 8,361,062 B2 | 1/2013 | Bonn |
| 8,394,086 B2 | 3/2013 | Behnke et al. |
| 8,394,087 B2 | 3/2013 | Willyard et al. |
| 8,394,092 B2 | 3/2013 | Brannan |
| 8,409,188 B2 | 4/2013 | Kim et al. |
| D681,810 S | 5/2013 | DeCarlo |
| 8,435,237 B2 | 5/2013 | Bahney |
| 8,463,396 B2 | 6/2013 | Podhajsky |
| 8,473,077 B2 | 6/2013 | Bonn et al. |
| 8,491,579 B2 | 7/2013 | Rossetto |
| 9,192,437 B2 * | 11/2015 | Brannan ................ A61B 18/18 |
| 9,662,172 B2 * | 5/2017 | Brannan ................ A61B 18/18 |
| 2002/0022836 A1 | 2/2002 | Goble et al. |
| 2003/0032951 A1 | 2/2003 | Rittman et al. |
| 2003/0153908 A1 | 8/2003 | Goble et al. |
| 2004/0049254 A1 | 3/2004 | Longo |
| 2004/0097805 A1 | 5/2004 | Verard et al. |
| 2004/0242992 A1 | 12/2004 | Hareyama |
| 2005/0015081 A1 | 1/2005 | Turovskiy et al. |
| 2005/0149010 A1 | 7/2005 | Turovskiy et al. |
| 2005/0245920 A1 | 11/2005 | Vitullo et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2006/0293650 A1 | 12/2006 | Prakash et al. |
| 2008/0039709 A1 | 2/2008 | Karmarkar |
| 2008/0119919 A1 | 5/2008 | Atalar et al. |
| 2009/0187180 A1 | 7/2009 | Brannan |
| 2009/0222002 A1 | 9/2009 | Bonn et al. |

(56) References Cited

U.S. PATENT DOCUMENTS

| | | |
|---|---|---|
| 2009/0248005 A1 | 10/2009 | Rusin et al. |
| 2009/0248006 A1 | 10/2009 | Paulus et al. |
| 2009/0295674 A1 | 12/2009 | Bonn |
| 2009/0306652 A1 | 12/2009 | Buysse et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0053015 A1 | 3/2010 | Willyard |
| 2010/0076422 A1 | 3/2010 | Podhajsky |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0114086 A1 | 5/2010 | Deem et al. |
| 2010/0256624 A1 | 10/2010 | Brannan et al. |
| 2010/0262134 A1 | 10/2010 | Jensen et al. |
| 2010/0268220 A1 | 10/2010 | Johnson et al. |
| 2010/0305559 A1 | 12/2010 | Brannan et al. |
| 2010/0305560 A1 | 12/2010 | Peterson |
| 2011/0034913 A1 | 2/2011 | Brannan |
| 2011/0034917 A1 | 2/2011 | Brannan |
| 2011/0040300 A1 | 2/2011 | Brannan |
| 2011/0060326 A1 | 3/2011 | Smith et al. |
| 2011/0066144 A1 | 3/2011 | Bonn et al. |
| 2011/0071582 A1 | 3/2011 | Willyard et al. |
| 2011/0077633 A1 | 3/2011 | Bonn et al. |
| 2011/0077634 A1 | 3/2011 | Brannan |
| 2011/0077637 A1 | 3/2011 | Brannan |
| 2011/0077638 A1 | 3/2011 | Brannan |
| 2011/0077639 A1 | 3/2011 | Brannan et al. |
| 2011/0118721 A1 | 5/2011 | Brannan |
| 2011/0196362 A1 | 8/2011 | Rossetto |
| 2011/0208177 A1 | 8/2011 | Brannan |
| 2011/0238054 A1 | 9/2011 | Kim et al. |
| 2011/0238055 A1 | 9/2011 | Kim et al. |
| 2011/0282336 A1 | 11/2011 | Brannan et al. |
| 2011/0295245 A1 | 12/2011 | Willyard et al. |
| 2011/0295246 A1 | 12/2011 | Prakash et al. |
| 2011/0319880 A1 | 12/2011 | Prakash et al. |
| 2012/0022622 A1 | 1/2012 | Johnson et al. |
| 2012/0029503 A1 | 2/2012 | Bonn |
| 2012/0172860 A1 | 7/2012 | Brannan |
| 2012/0172861 A1 | 7/2012 | Brannan |
| 2012/0172862 A1 | 7/2012 | Brannan |
| 2012/0172863 A1 | 7/2012 | Brannan |
| 2012/0194409 A1 | 8/2012 | Brannan et al. |
| 2012/0203217 A1 | 8/2012 | Brannan |
| 2012/0232544 A1 | 9/2012 | Willyard et al. |
| 2012/0232549 A1 | 9/2012 | Willyard et al. |
| 2012/0259324 A1 | 10/2012 | Brannan |
| 2012/0259329 A1 | 10/2012 | DeCarlo |
| 2012/0310228 A1 | 12/2012 | Bonn et al. |
| 2012/0330302 A1 | 12/2012 | Willyard |
| 2013/0030429 A1 | 1/2013 | Rusin |
| 2013/0041362 A1 | 2/2013 | Lee et al. |
| 2013/0041365 A1 | 2/2013 | Rusin et al. |
| 2013/0053695 A1 | 2/2013 | Brannan |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079765 A1 | 3/2013 | Kim et al. |
| 2013/0085488 A1 | 4/2013 | Brannan et al. |
| 2013/0103025 A1 | 4/2013 | Brannan |
| 2013/0103029 A1 | 4/2013 | Brannan |
| 2013/0110102 A1 | 5/2013 | Prakash et al. |
| 2013/0123772 A1 | 5/2013 | Bonn et al. |
| 2013/0126207 A1 | 5/2013 | Rossetto et al. |
| 2013/0131670 A1 | 5/2013 | Prakash |
| 2013/0178841 A1 | 7/2013 | Reid, Jr. |
| 2013/0178842 A1 | 7/2013 | Reid, Jr. |
| 2013/0178843 A1 | 7/2013 | Lee et al. |
| 2013/0178844 A1 | 7/2013 | Lee et al. |
| 2013/0190749 A1 | 7/2013 | Willyard et al. |
| 2013/0190751 A1 | 7/2013 | Brannan |
| 2013/0192063 A1 | 8/2013 | Brannan |
| 2013/0218143 A1 | 8/2013 | Ross |
| 2013/0226172 A1 | 8/2013 | Peterson et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0481685 A1 | 4/1992 |
| EP | 0521264 A2 | 1/1993 |
| EP | 556705 A1 | 8/1993 |
| EP | 0558429 A1 | 9/1993 |
| EP | 0572131 A1 | 12/1993 |
| EP | 0648515 A1 | 4/1995 |
| EP | 0541930 B1 | 3/1998 |
| EP | 836868 A2 | 4/1998 |
| EP | 882955 A1 | 12/1998 |
| EP | 1034748 A1 | 9/2000 |
| EP | 1055400 A1 | 11/2000 |
| EP | 1278007 A1 | 1/2003 |
| EP | 1159926 A3 | 3/2003 |
| EP | 1810627 A1 | 7/2007 |
| EP | 2060239 A1 | 5/2009 |
| EP | 2128929 A1 | 12/2009 |
| EP | 2158868 A1 | 3/2010 |
| EP | 2177173 A1 | 4/2010 |
| EP | 2255742 A1 | 12/2010 |
| EP | 2399646 A1 | 12/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |

(56) References Cited

FOREIGN PATENT DOCUMENTS

| | | |
|---|---|---|
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 2001003776 A | 1/2001 |
| JP | 200129356 | 2/2001 |
| JP | 200137775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 9735639 A1 | 10/1997 |
| WO | 9741924 A1 | 11/1997 |
| WO | 9743971 A2 | 11/1997 |
| WO | 0036985 A2 | 6/2000 |
| WO | 0048672 A1 | 8/2000 |
| WO | 0051513 A1 | 9/2000 |
| WO | 0053112 A2 | 9/2000 |
| WO | 0101847 A1 | 1/2001 |
| WO | 0174252 A2 | 10/2001 |
| WO | 0245790 A2 | 6/2002 |
| WO | 2002061880 A2 | 8/2002 |
| WO | 03039385 A2 | 5/2003 |
| WO | 2004/112628 A1 | 12/2004 |
| WO | 2005011049 A2 | 2/2005 |
| WO | 2005016119 A2 | 2/2005 |
| WO | 2006084676 A1 | 8/2006 |
| WO | 2008131302 A2 | 10/2008 |
| WO | 2009075879 A1 | 6/2009 |
| WO | 2009075904 A1 | 6/2009 |
| WO | 2009094422 A1 | 7/2009 |
| WO | 2010035831 A1 | 4/2010 |

OTHER PUBLICATIONS

European Search Report dated Oct. 17, 2017 issued in European Application No. 17179325.0.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
Goldberg et al. (1995) "Saline-enhanced RF Ablation: Demonstration of Efficacy and Optimization of Parameters", Radiology, 197(P): 140 (Abstr).
Johnson et al., "New Low-Profile Applicators for Local Heating of Tissues", IEEE Transactions on Biomedical Engineering, vol. BME-31, No. 1, Jan. 1984, pp. 28-37.
Solbiati et al. (1995) "Percutaneous US-guided RF Tissue Ablation of Liver Metastases: Long-term Follow-up", Radiology, pp. 195-203.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.

(56) References Cited

OTHER PUBLICATIONS

Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, CarolinasMedicalCenter,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw. cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
Australian Examination Report No. 2 issued in Appl. No. 2017202181 dated Apr. 21, 2018 (2 pages).
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019178.8 dated Feb. 12, 2008.
European Search Report EP 07019174.7 dated Jan. 29, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.

(56) References Cited

OTHER PUBLICATIONS

U.S. Appl. No. 13/836,353, filed Mar. 15, 2013, Arts.
U.S. Appl. No. 13/839,562, filed Mar. 15, 2013, Zheng.
U.S. Appl. No. 13/853,363, filed Mar. 29, 2013, Kim.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery vol. 181, No. 3, OApr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite.Element Codes to Model Electrical Heating and Non.cndot.L1near Thermal Transport in Biological Media", Proc. ASME HTD-355, 131 (1997).
Esterline Product Literature, "Light Key: Visualize a Virtual Keyboard. One With No Moving Parts". Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 081699718 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1991.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation—COA-COMP" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 047523416 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
Japanese Office Action for application No. 2015-204490 dated Sep. 14, 2016.
Australian Examination Report for application No. 2015204318 dated Sep. 18, 2016.

\* cited by examiner

NARROW GAUGE HIGH STRENGTH CHOKED WET TIP MICROWAVE ABLATION ANTENNA

CROSS-REFERENCE TO RELATED APPLICATION

This application is a continuation of U.S. patent application Ser. No. 14/931,922, filed on Nov. 4, 2015, now U.S. Pat. No. 9,662,172, which is a continuation of U.S. patent application Ser. No. 13/657,638, filed on Oct. 22, 2012, now U.S. Pat. No. 9,192,437, which is a continuation of U.S. patent application Ser. No. 12/472,831, filed on May 27, 2009, now U.S. Pat. No. 8,292,881, the entire contents of each of which are hereby incorporated by reference herein.

BACKGROUND

1. Technical Field

The present disclosure relates to systems and methods for providing energy to biological tissue and, more particularly, to a microwave ablation surgical probe having a concentric tubular structure and conical distal tip, and methods of use and manufacture therefor.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Microwave energy can be delivered to tissue using an antenna probe. Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

A typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, more narrow ablation volume, whereas in a prostate ablation procedure, a more spherical ablation volume may be required.

In some surgical procedures, a microwave antenna probe may be inserted percutaneously into, for example, a chest wall of a patient. During such a procedure, negotiating the probe through, for example, fibrous thoracic tissue and ribs may place undue stresses on the probe. Additionally, microwave energy may radiate into the skin, which may increase the likelihood of complications, such as skin burn.

SUMMARY

The present disclosure provides an electromagnetic surgical ablation probe having a cooled and dielectrically buffered antenna assembly. A cable provides electromagnetic energy to the probe via a coaxial conductor and/or provides coolant via a fluid conduit to improve power delivery performance and power handling, and to reduce component temperatures. Suitable coolants include deionized water, sterile water, or saline.

The probe includes two concentrically-disposed cylindrical tubes. An outer tube is a catheter formed from a radiofrequency transparent material such as an epoxy glass composite and extends from a proximal device handle to a distal tip of the probe. The catheter radiofrequency transparent material may additionally have a low electrical conductivity, or dielectric properties. In an embodiment, the catheter material may exhibit a low electrical conductivity, or dielectric properties, at a probe operating frequency (e.g., 915 MHz to 2.45 GHz). An inner tube is formed from conductive material, e.g., a metal such as stainless steel, and extends from the device handle to a proximal end of the radiating section. The inner diameter of the outer tube is substantially equal to the outer diameter of the inner tube.

A metal or plastic tip may be positioned at a distal end of the catheter. The tip may be made with trocar geometry (e.g., substantially conical) to improve ease of insertion of the probe into tissue. The tip and catheter may be coated with non-stick heat shrink material and/or lubricious coating.

An electrical connection is made between the inner metal tube and the outer conductor of the coaxial feedline at a distance of about one-quarter wavelength (λ/4) proximally from a distal end of the metal inner tube, forming a short circuited balun. Alternatively, the balun may be positioned at any odd multiple of one-quarter wavelengths (e.g., 3λ/4, 5λ/4, etc.) from a distal end of the inner metal tube. As used herein, the term wavelength refers to the wavelength of electromagnetic energy, e.g., microwave ablation energy, corresponding to an operating frequency of the disclosed antenna. The circulating coolant, which preferably has low conductivity, forms the dielectric insulator of the balun.

The radiating section of the antenna has a dipole structure. The dipole feed is constructed by opening (e.g., stripping) the coaxial outer conductor and exposing an extended dielectric and inner conductor of the coaxial feedline distally. The coaxial dielectric truncation coincides with the inner conductor increasing in diameter at a cylindrical radiating section that extends further distally toward the distal tip of the antenna. The inner conductor may be directly coupled to the tip of the antenna. The inner conductor may also flare, spiral or be loaded with disks to improve radiating performance and provide additional mechanical strength.

Notches in the balun short permit fluid circulation through the balun structure into the radiating section for cooling and dielectric buffering. Screening or mesh may also be used for the balun short. Fluid inflow and outflow control may be accomplished by either using inflow and/or outflow tubes which pass through the short circuit into the radiating section, or by using a extruded low conductivity structure to divide the cylindrical geometry into two sections for inflow and outflow. The structure may additionally center the coaxial feed line and antenna radiating structure within the catheter tubes.

A microwave ablation antenna according to the present disclosure may have advantages, such as quickly achieving a large ablation diameter, a nearly spherical ablation shape, low reflected power, cool probe shaft, with a narrower gauge needle size (15 g) for use in percutaneous procedures. The metal conductive tube may provide increased strength and stiffness, which permits difficult insertion through, for example, the chest wall. The balun short may confine most radiation to the distal tip of the probe, reducing the likelihood of complications from multiple antenna interactions, which may cause skin burn In one embodiment, an electromagnetic surgical ablation probe according to the present disclosure includes a coaxial feedline having an inner conductor, outer conductor and a dielectric disposed therebetween. The outer conductor is truncated (e.g., stripped), whereby the inner conductor and dielectric extend beyond the outer conductor. A radiating section is coupled to the distal end of the inner conductor, and a distal tip is coupled to a distal end of the radiating section. The tip includes a generally cylindrical proximal tip extension having at least one o-ring disposed thereabout, which may help seal the coolant chamber from fluid leakage. The disclosed probe also includes a ring-like balun short disposed in electrical communication around the outer conductor, which may help control a radiation pattern of the probe. A conductive tube disposed therethrough. A radiofrequency transparent catheter joined to a proximal end of the distal tip encloses the probe and defines a coolant chamber within the probe.

Also disclosed is an electromagnetic surgical ablation system which includes a source of microwave ablation energy operably coupled to the aforementioned probe by a coaxial feedline.

The present disclosure is also directed to a method of manufacturing a microwave ablation probe that includes the steps of providing a coaxial feedline having an inner conductor, an outer conductor, and a dielectric disposed therebetween. A distal radiating section cylinder is joined to a distal end of the inner conductor and a distal tip is joined to the distal radiating section cylinder. A balun short having at least one notch defined therein is positioned on the outer conductor, and at least one fluid conduit member is positioned on an outer surface of the outer conductor such that the fluid conduit member is longitudinally disposed within the notch provided on the balun short. A conductive tube is positioned around the balun short, and radiofrequency transparent conduit is positioned over the assembly. A distal end of the radiofrequency transparent conduit is fixed to a proximal end of the distal tip.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
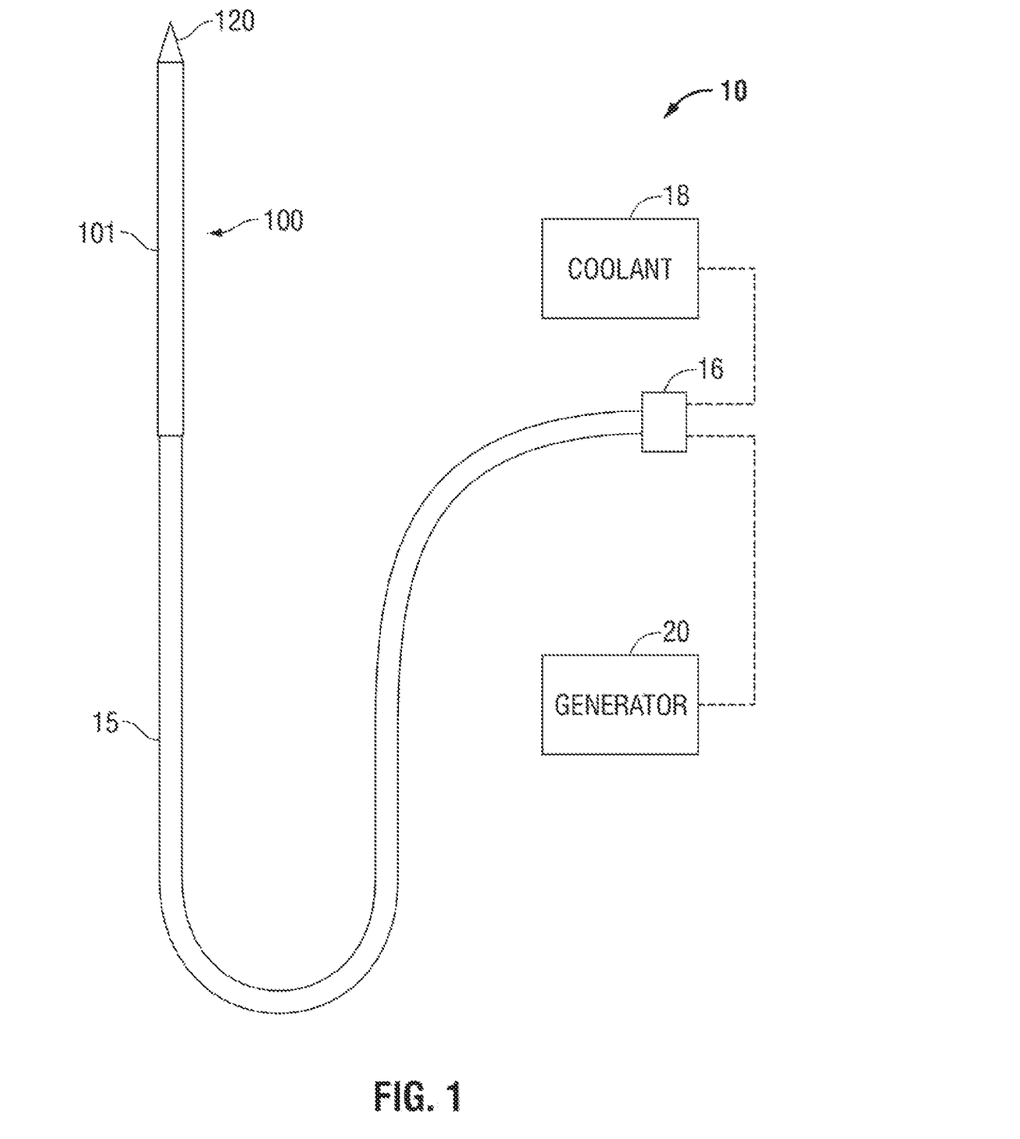
FIG. 1 shows a diagram of a microwave ablation system having an electromagnetic surgical ablation probe in accordance with the present disclosure.

FIG. 1 shows an embodiment of a microwave ablation system 10 in accordance with the present disclosure. The microwave ablation system 10 includes an electromagnetic surgical ablation probe 100 connected by a cable 15 to connector 16, which may further operably connect the probe 100 to a generator assembly 20. Generator assembly may be a source of ablation energy, e.g., microwave or RF energy in the range of about 915 MHz to about 2.45 GHz. Cable 15 may additionally or alternatively provide a conduit (not explicitly shown) configured to provide coolant from a coolant source 18 to the electromagnetic surgical ablation probe 100.

In greater detail, and with reference to FIG. 2 and FIGS. 3A-3D, an embodiment of an electromagnetic surgical ablation probe 100 includes a shaft assembly 101 having a coaxial feedline 102 disposed through the longitudinal axis of the shaft 101. The feedline 102 includes an inner conductor 103 disposed coaxially within an outer conductor 105 and a dielectric (e.g., insulator) 104 concentrically disposed between the inner conductor 103 and outer conductor 105. In embodiments, feedline 102 has a nominal impedance of about 50 ohms. Inner conductor 103 and dielectric 104 extend beyond outer conductor 105 at a distal end of feedline 102.

A distal radiating section cylinder 124 is coupled to a distal end of the inner conductor 103. A distal tip 120 is coupled at a proximal end 121 thereof to a proximal tip extension 131. In an embodiment, proximal tip extension 131 and distal tip 120 may be integrally formed. In yet another embodiment, distal radiating section cylinder 124 may be formed from two sections wherein a proximal section is coupled to a distal end of the inner conductor 103, and a distal section is integrally formed with proximal tip extension 131. Inner conductor 103, distal radiating section cylinder 124, proximal tip extension 13 land distal radiating section cone 120 may be respectively coupled by any suitable manner of bonding, including without limitation welding, soldering, crimping, or threaded fastening. A proximal end of feedline 102 may be operably coupled to a generator 20 configured to generate microwave ablation energy in the range of about 800 MHz to about 5 GHz.

Figure 2:
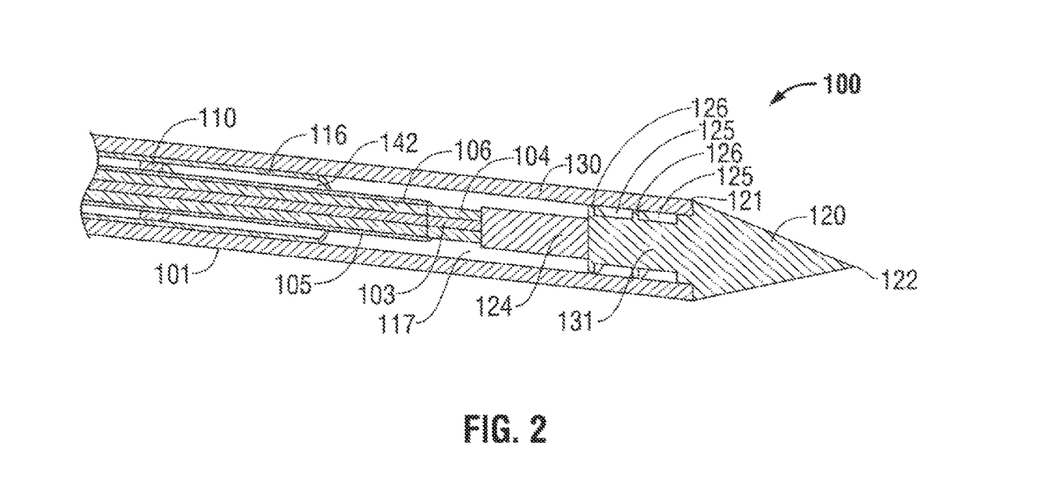
FIG. 2 shows a cross sectional view of an embodiment of an electromagnetic surgical ablation probe in accordance with the present disclosure.

In one embodiment, distal tip 120 has a generally conical shape having an apex at a distal end 122 thereof. However, embodiments are envisioned wherein distal tip 120 may have any shape, including without limitation, a cylindrical, rounded, parabolic, flat, knife-like, and/or flared shape. Distal tip 120 may be formed from any suitable material, include metallic, nonmetallic, and polymeric materials.

With reference particularly to FIG. 3D, at least one o-ring 126 is positioned around distal radiating section cylinder 124 and/or a distal segment thereof that is integrally formed with distal tip 120. O-ring 126 may be formed from any suitable heat-resistant material, and may additionally or alternatively be integrally formed with distal radiating section cylinder 124 and/or a distal segment thereof that is integrally formed with distal tip 120. An outer diameter of o-ring 126 is dimensioned to provide a fluid seal with an inner diameter of catheter 130 as illustrated in FIGS. 4C and 5B and as will be described in greater detail below. Distal tip 120 may include at a proximal end thereof a shoulder 123 that has an outer diameter dimensioned to couple with an inner diameter of conductive tube 116. Additionally or alternatively, shoulder 123 may include an o-ring 126. In one embodiment, a sealant (not explicitly shown) such as elastomeric polymer or epoxy may be included in a region 125 adjacent to o-ring 126 and/or shoulder 123.

Figure 6:
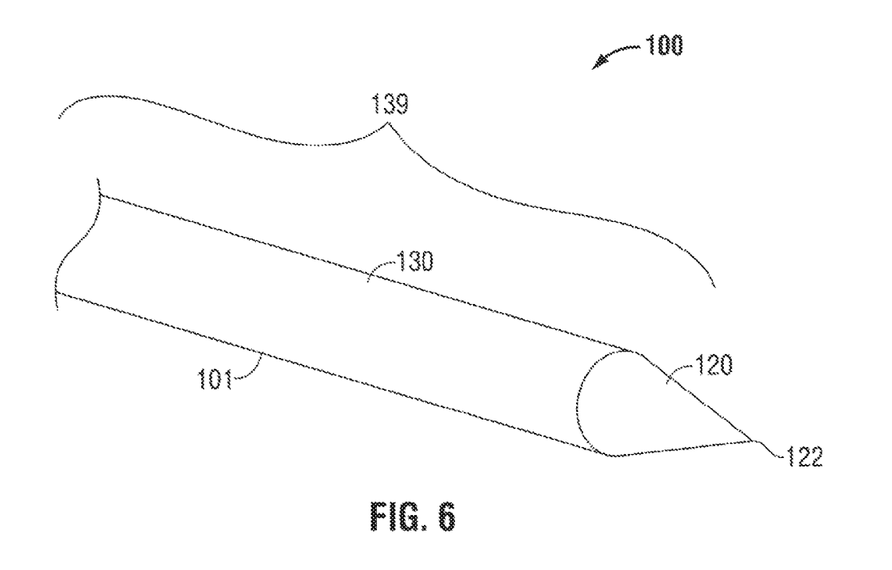
FIG. 6 shows an external perspective view of an embodiment of an electromagnetic surgical ablation probe in accordance with the present disclosure.

Referring again to FIG. 2, and to FIG. 6, a tubular catheter 130 extends proximally from a proximal end 121 of distal tip 120. Catheter 130 has an inner diameter substantially equal to the outer diameter of a conductive tube 116 and of shoulder 123. An outer diameter of catheter 130 has an outer diameter that substantially corresponds to that of the base (e.g., proximal) diameter of distal tip 120. Catheter 130 is formed from radiofrequency transparent material. Catheter 130 may be formed from material having a low electrical conductivity, or dielectric properties. In an embodiment, the probe 130 material may have low electrical conductivity, or dielectric properties, in a probe operating frequency range, e.g., an operating range of about 915 MHz to about 2.45 GHz. Catheter 130 may be formed from composite material, such as without limitation, epoxy glass composite, carbon fiber, and the like. In an embodiment, catheter 130 may not be completely transparent to radiofrequency energy, and instead may be nearly or substantially transparent. In use, a dielectric constant of catheter 130 may aid in matching the combined impedance of the probe and tissue in contact therewith to the impedance of coaxial feedline 102, which in turn may improve energy delivery to tissue. Additionally, the low electrical conductivity of catheter 130 may reduce undesired reflection of radiofrequency and/or microwave energy.

Figure 3A:
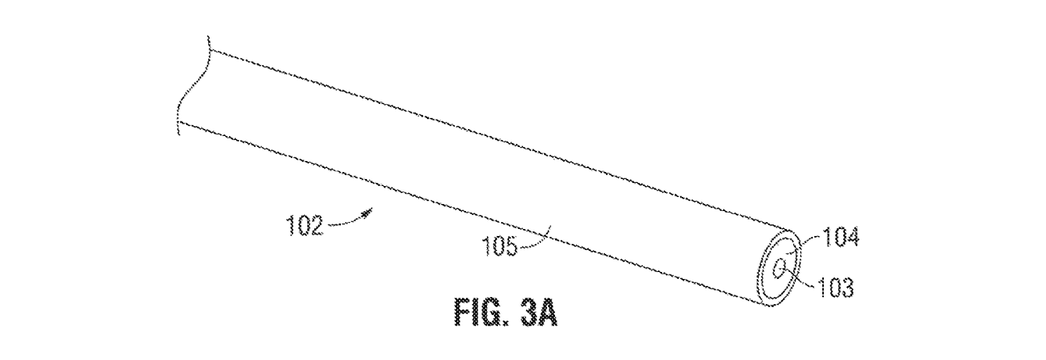
FIGS. 3A-3E show perspective views of an embodiment of an electromagnetic surgical ablation probe at various stages of assembly in accordance with the present disclosure.
Figure 3B:
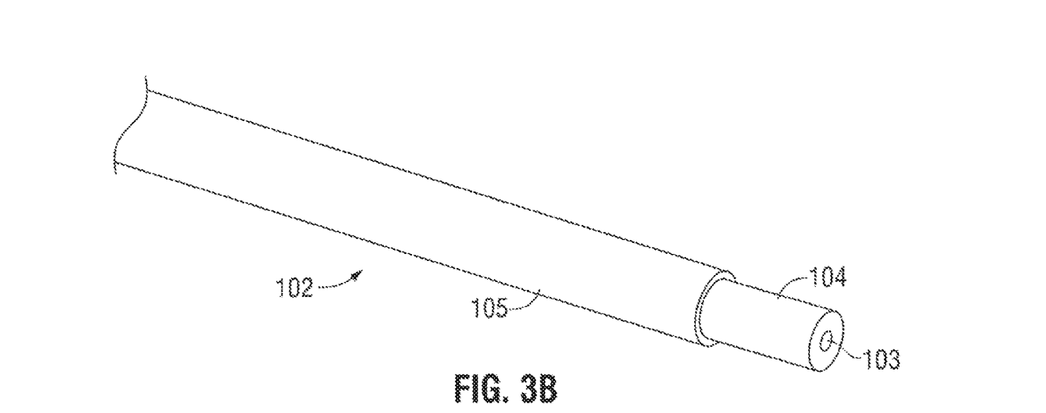
Figure 3C:
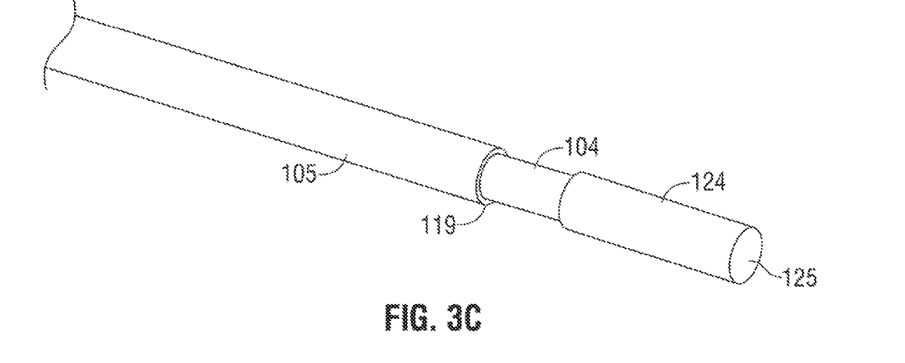
Figure 3D:
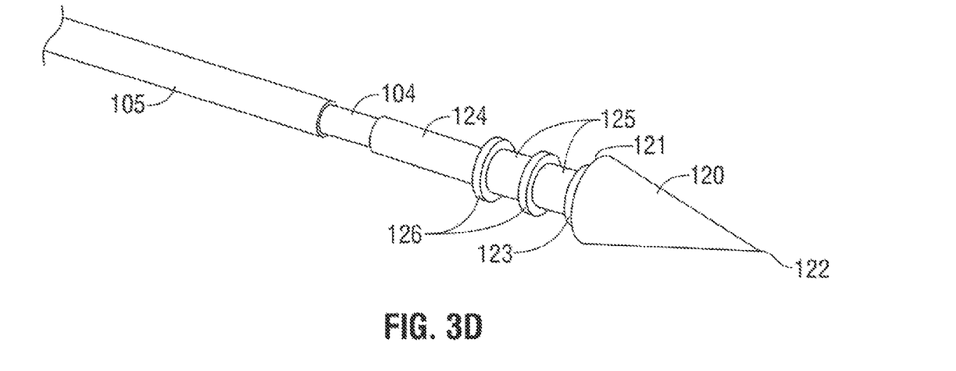
Figure 3E:
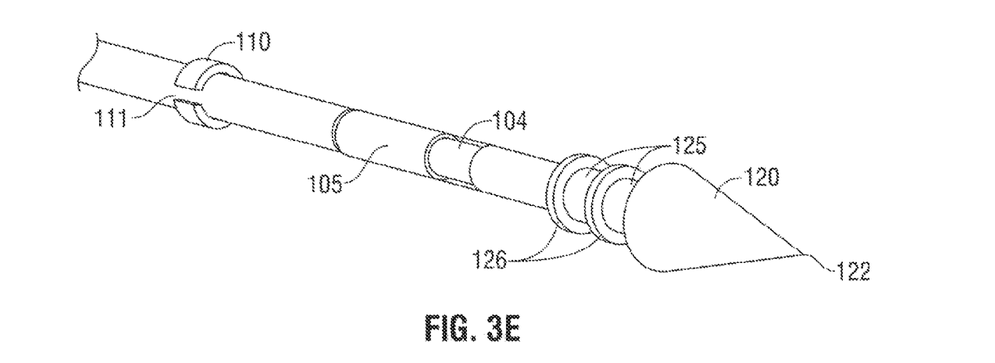

The disclosed probe includes a balun short 110 that is coaxially disposed around a outer conductor, located proximally of a distal end 119 of outer conductor as best seen in FIG. 3E. Advantageously, balun short 110 may be positioned a quarter wavelength distance from a distal end 119 of conductive tube 116. Balun short 110 may be formed from conductive material (e.g., metallic or conductive polymeric material) to form an electrical connection between outer conductor 105 and conductive tube 116. Balun short 110 includes at least one notch 111 defined therein which may assist in cooling the probe 100 during use. A coolant chamber 117 may be defined by the inner surface of catheter 130, o-ring 126, balun short 110, and the outer surface of outer conductor 105. Balun short 110 may additionally or alternatively be formed from conductive screen, mesh or woven materials. In embodiments, cooling may be achieved passively by thermal convection (e.g., ventilation provided by the at least one notch 111), or actively by the flow of coolant within the probe 100 as will now be described. Catheter 130 and/or distal tip 120 may include a coating (not explicitly shown), such as a lubricious (e.g., non-stick) coating formed from polytetrafluoroethylene (a.k.a. PTFE or Teflon®, manufactured by the E.I. du Pont de Nemours and Co. of Wilmington, Del., USA), polyethylene tephthalate (PET), or the like. Additionally or alternatively, catheter 130 and/or distal tip 120 may include a heat shrink coating, such as polyolefin tubing or any suitable heat-shrink material.

Figure 4A:
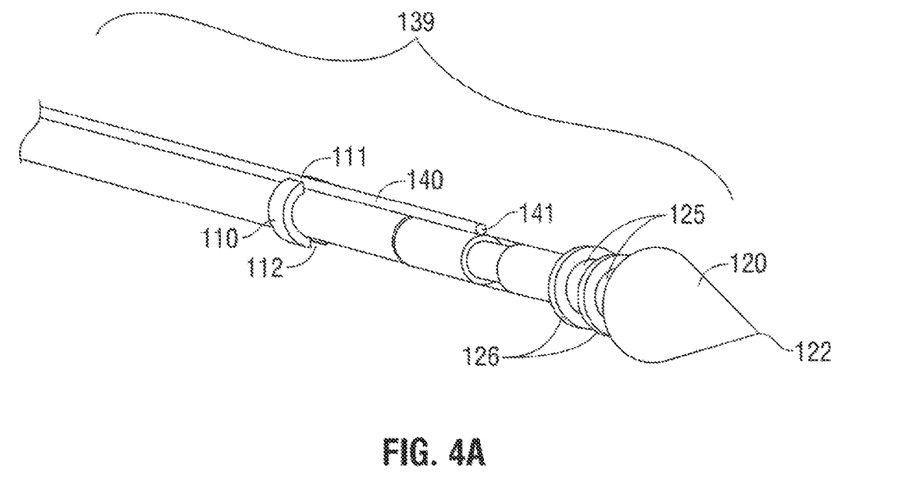
FIGS. 4A-4B show views of another embodiment of an electromagnetic surgical ablation probe at various stages of assembly in accordance with the present disclosure.
Figure 4B:
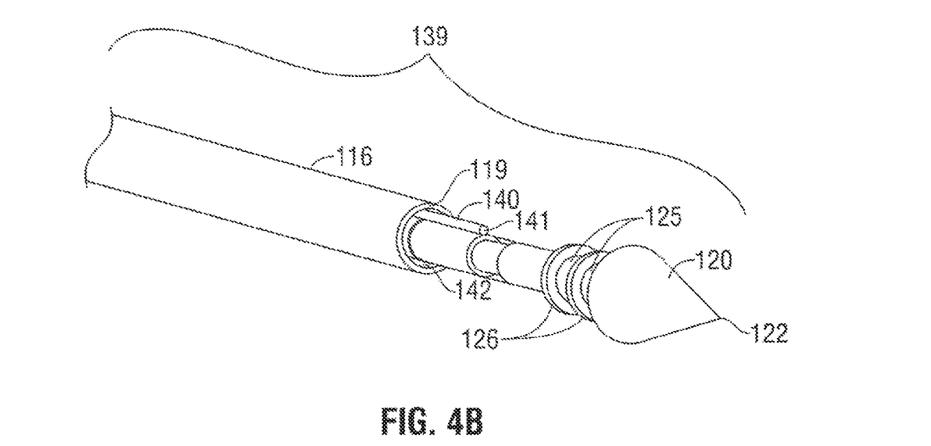

In an embodiment illustrated in FIGS. 4A and 4B, an inflow tube 140 is disposed longitudinally along an outer surface of outer conductor 105. Inflow tube 140 includes an open distal end 141 that is configured to deliver coolant fluid to a coolant chamber 117. Inflow tube 140, at a proximal end thereof (not explicitly shown), may be in fluid communication with a coolant source 18, such as without limitation a coolant pump or drip bag. Any suitable medium may be used as a coolant. In embodiments, deionized water, sterilized water, or saline may be used as a coolant. In one aspect, the coolant may have dielectric properties which may provide improved ablation volume and shape, and/or may provide improved impedance matching between the probe 100 and tissue. During use, coolant flows distally though inflow tube 140 and is introduced into coolant chamber 117 at the open distal end 141 of inflow tube. As best seen in FIG. 4A, inflow tube 140 is positioned within notch 111 defined in balun short 110. Balun short 110 includes an outflow notch 112 through which coolant may exit coolant chamber 117.

Figure 5A:
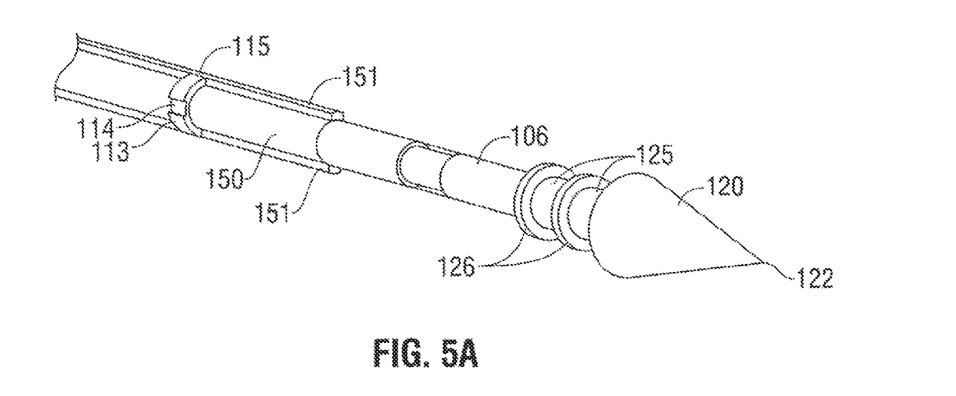
FIGS. 5A-5C show views of yet another embodiment of an electromagnetic surgical ablation probe at various stages of assembly in accordance with the present disclosure.
Figure 5B:
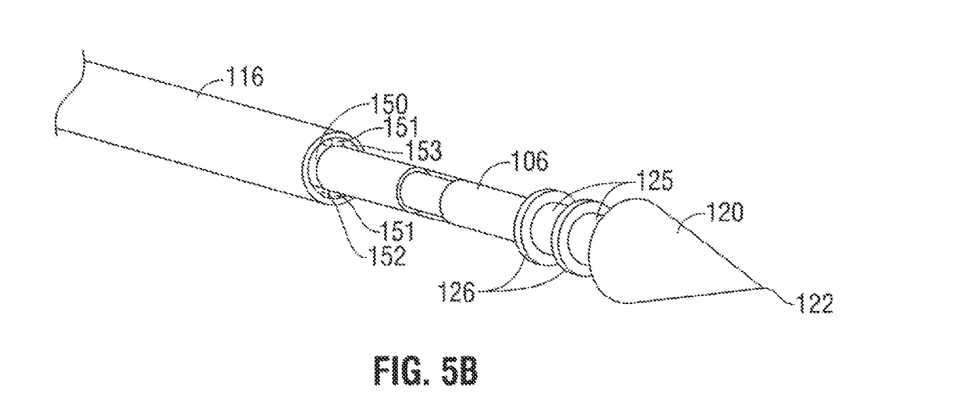
Figure 5C:
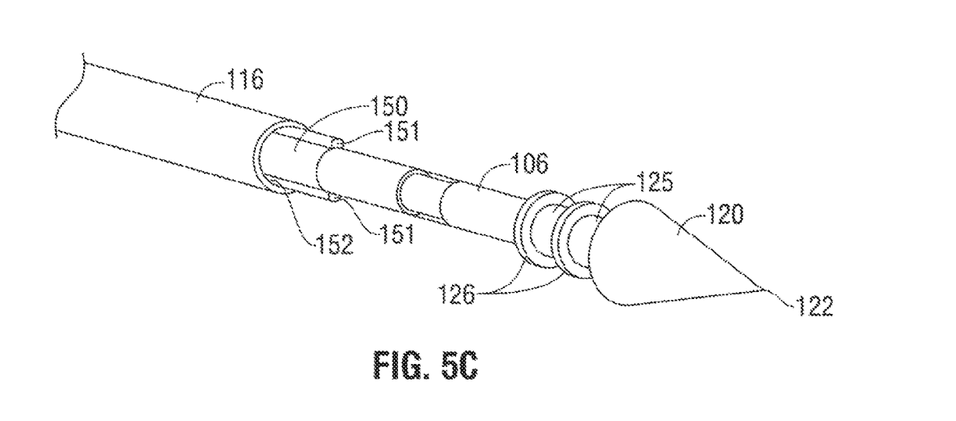

In another embodiment illustrated in FIGS. 5A, 5B, and 5C, a rib 151 is longitudinally disposed between an outer surface of outer conductor 105 and conductive tube 116 to concentrically position coaxial feedline 102 within conductive tube. Rib 151 is preferably formed from a low-conductivity or insulating material. A second longitudinal rib 151 may be included to form an inflow channel 152 and an outflow channel 153. The ribs 151 may radially opposed (e.g., offset approximately 180° apart as indexed with reference to the circular cross-section of coaxial feedline 102 and/or conductive tube 116) and dimensioned to define an inflow channel 152 and outflow channel 153 between conductive tube 116 and outer conductor 105 of substantially similar size. Embodiments are envisioned within the scope of the present disclosure wherein ribs 151 are positioned more, or less, than 180° apart. Embodiments having three or more ribs are contemplated, wherein three or more channels (not explicitly shown) are formed. The additional channels may be used to circulate different types of coolant, having, for example, differing dielectric and/or thermal properties. Additionally, the channels may deliver to the probe, and/or to tissue, medicaments, bioadhesives, radioisotopes, and/or other useful therapeutic compounds. With particular reference to FIG. 5A, the present embodiment includes a balun short 113 having rib notches 115 that are adapted to position and retain ribs 151. Balun short 113 additionally includes coolant notches 114 that are adapted to facilitate the flow of coolant past balun short 113, as will be readily appreciated. In embodiments, balun short 113 may be constructed from perforated metal, metal mesh, or screen material.

A method of manufacturing a high-strength microwave ablation probe 100 is shown in accordance with the present disclosure with reference now to FIGS. 3A-3E. It is to be understood that the steps of the method provided herein may be performed in combination and in a different order than presented herein without departing from the scope and spirit of the present disclosure.

With reference to FIG. 3A, a coaxial feedline 102 is provided having an inner conductor 103, a dielectric 104 and an outer conductor 105. As shown in FIG. 3B, the inner conductor 103 and dielectric 104 is extended beyond outer conductor 105 at a distal end thereof. In one embodiment of the disclosed method, a stripping tool may be used to trim a distal portion of outer conductor 105 to expose inner conductor 103 and dielectric 104. As seen in FIG. 3C, a distal radiating section cylinder 124 is provided and affixed to inner conductor 103 by any suitable manner of attachment, for example and without limitation, by laser welding. As shown in Fig, 3D, a distal tip 120 is provided, having a generally conical shape and including a proximal tip extension 131 that is dimensioned to couple to a distal surface 129 of distal radiating section cylinder 124. Distal tip 120 is affixed to distal radiating section cylinder 124 by any suitable manner of bonding, such as without limitation, by laser welding or threaded fastener. At least one o-ring 126 is positioned on proximal tip extension 131. In a step illustrated in FIG. 3E, a balun short 110 having a notch 111 defined therein is positioned and electrically coupled to outer conductor 105.

In an embodiment best illustrated in FIG. 4A, an inflow tube 140 is longitudinally disposed along outer conductor 105 and positioned within notch 111. As seen in FIG. 4B, a conductive tube 116 is positioned over the assembly 139. A distal end 119 of conductive tube 116 is positioned distally of balun short 110 at a distance of about one-quarter wavelength therefrom. In a step depicted in FIG. 6, catheter 130 is positioned over the assembly 139 and joined to a proximal end 121 of tip 120. An inner diameter of catheter 130 may be dimensioned to engage an outer diameter of shoulder 123. Additionally or alternatively, a sealant (not explicitly shown) may be applied to region 125 adjacent to o-ring 126 and/or shoulder 123.

In an embodiment best illustrated in FIG. 5A, a balun short 113 having two pairs of radially opposed notches 114, 115 defined therein is positioned and electrically coupled to outer conductor 105. A pair of ribs 151 are longitudinally positioned within a respective notch 115. A distal end 119 of conductive tube 116 is positioned distally of balun short 110 at a distance of about one-quarter wavelength therefrom. In a step depicted in FIG. 6, catheter 130 is positioned over the assembly and joined to a proximal end 121 of tip 120. An inner diameter of catheter 130 may be dimensioned to engage an outer diameter of shoulder 123. Additionally or alternatively, a sealant (not explicitly shown) may be applied to region 125 adjacent to o-ring 126 and/or shoulder 123.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An ablation probe, comprising:
   a tubular shaft;
   a coaxial feedline disposed within the tubular shaft, the coaxial feedline including an outer conductor;
   a balun short disposed in electrical communication around the outer conductor, the balun short including at least one longitudinal notch defined therein; and
   an inflow tube disposed longitudinally along the outer conductor and at least partially within the at least one longitudinal notch.

2. The ablation probe according to claim 1, wherein the balun short is formed from a conductive material selected from the group consisting of a screen material, a mesh material, and a woven material.

3. The ablation probe according to claim 1, wherein the balun short is formed from a conductive material selected from the group consisting of a metallic material and a polymeric material.

4. The ablation probe according to claim 1, wherein the coaxial feedline further includes an inner conductor and the outer conductor is disposed coaxially about the inner conductor.

5. The ablation probe according to claim 4, wherein the coaxial feedline further includes a dielectric disposed between the inner conductor and the outer conductor and the inner conductor and the dielectric extend beyond a distal end of the outer conductor.

6. The ablation probe according to claim 5, further comprising a radiating section having a proximal portion operably coupled to a distal portion of the inner conductor.

7. An ablation system, comprising:
   a source of microwave ablation energy; and
   an ablation probe including:
      a tubular shaft;
      a coaxial feedline disposed within the tubular shaft, the coaxial feedline coupled to the source of microwave ablation energy and including an outer conductor;
      a balun short disposed in electrical communication around the outer conductor, the balun short including at least one longitudinal notch defined therein; and
      an inflow tube disposed longitudinally along the outer conductor and at least partially within the at least one longitudinal notch.

8. The ablation system according to claim 7, further comprising a plurality of rib members, wherein the balun short includes a plurality of additional longitudinal notches defined therein adapted to receive a corresponding rib member of the plurality of rib members.

9. The ablation system according to claim 8, wherein the plurality of rib members divide the at least one fluid conduit into at least two longitudinal channels.

10. The ablation system according to claim 7, wherein the balun short is formed from a conductive material selected from the group consisting of a screen material, a mesh material, and a woven material.

11. The ablation system according to claim 7, wherein the balun short is formed from a conductive material selected from the group consisting of a metallic material and a polymeric material.

12. The ablation system according to claim 7, wherein the coaxial feedline further includes an inner conductor and the outer conductor is disposed coaxially about the inner conductor.

13. The ablation system according to claim 12, wherein the coaxial feedline further includes a dielectric disposed between the inner conductor and the outer conductor and the inner conductor and the dielectric extend beyond a distal end of the outer conductor.

14. The ablation system according to claim 13, further comprising a radiating section having a proximal portion operably coupled to a distal portion of the inner conductor.

* * * * *